United States Patent [19]

Iwakura et al.

[11] Patent Number: 4,535,348

[45] Date of Patent: Aug. 13, 1985

[54] FLUORAN DERIVATIVES AND RECORDING MATERIAL USING SAME

[75] Inventors: Ken Iwakura; Sadao Ishige, both of Kanagawa, Japan

[73] Assignee: Fuji Photo Film Co., Ltd., Kanagawa, Japan

[21] Appl. No.: 395,237

[22] Filed: Jul. 6, 1982

[30] Foreign Application Priority Data

Jul. 6, 1981 [JP]  Japan ................... 56-105416

[51] Int. Cl.$^3$ .................. B41M 5/16; B41M 5/18; B41M 5/22
[52] U.S. Cl. .................. 346/221; 346/217; 427/150
[58] Field of Search ......... 282/27.5; 427/150, 151; 428/411, 537, 913, 914; 346/217, 221, 225; 549/226

[56] References Cited

U.S. PATENT DOCUMENTS 3,721,576  3/1973  Farber et al. .............. 282/27.5
3,825,432  7/1974  Futaki et al. .............. 106/21
3,825,561  7/1974  Akamatsu et al. ........... 549/226
3,929,831  12/1975  Garner et al. ............. 546/197

FOREIGN PATENT DOCUMENTS 2905825  8/1979  Fed. Rep. of Germany ...... 346/121

*Primary Examiner*—Bruce H. Hess
*Attorney, Agent, or Firm*—Sughrue, Mion, Zinn, Macpeak & Seas

[57] ABSTRACT

Fluoran derivatives having an arylamino group at 2-position of the fluoran skeleton thereof and a halogen atom at 3-position of the flouran skeleton thereof, useful as a dye precursor in recording materials such as heat-sensitive, pressure-sensitive, energizable heat-sensitive, and light-sensitive recording sheets and the like.

4 Claims, No Drawings

FLUORAN DERIVATIVES AND RECORDING MATERIAL USING SAME

FIELD OF THE INVENTION

This invention relates to novel fluoran derivatives which are extremely useful as dye precursors for use in recording materials such as pressure-sensitive recording sheets, heat-sensitive recording sheets, energizable heat-sensitive recording sheets, etc., and are also useful in light-sensitive recording sheets, ultrasonic wave-recording sheets, electron beam-recording sheets, electrostatic recording sheets, light-sensitive printing plate-making materials, stamping materials, typewriter ribbons, inks for ball-point pens, crayons, etc.

BACKGROUND OF THE INVENTION

U.S. Pat. No. 3,825,432, West German Patent OLS No. 2,262,127, and Japanese Patent Publication No. 38245/76 disclose various fluoran derivatives as dye precursors for pressure-sensitive paper or heat-sensitive paper. However, such known fluoran derivatives do not provide deep black images. In addition, the fluoran derivatives themselves are unstable in the atmosphere and dyes produced therefrom show poor fastness to light, humidity, etc.

SUMMARY OF THE INVENTION

It is, therefore, an object of the present invention to provide novel fluoran derivatives which are particularly excellent dye precursors for recording materials.

The above-described object of the present invention has been attained by fluoran derivatives having an arylamino group ($C_6$ to $C_{30}$) at the 2-position of the fluoran skeleton thereof and a halogen atom at 3-position of the fluoran skeleton thereof.

DETAILED DESCRIPTION OF THE INVENTION

The fluoran derivatives of the present invention are stable in the atmosphere and are colorless or slightly colored powders. When brought into an intimate contact with an electron accepting substance such as activated clay, a phenol-formaldehyde resin, an organic acid, an organic acid metal salt, bisphenol A, or the like, they essentially instantly form a black color. Their color forming ability is not deteriorated by coloration or decomposition during storage and thus, they have excellent properties as dye precursors for recording materials.

In particular, heat-sensitive recording materials containing the fluoran derivative of the present invention have a less colored background, suffer extremely slight fogging during storage and have excellent properties as compared to conventional materials.

Of the fluoran derivatives of the present invention, preferred examples are represented by the following general formula (I):

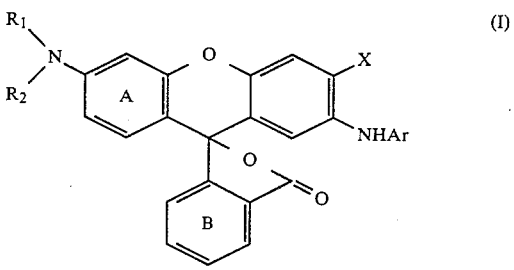

wherein $R_1$ and $R_2$, which may be the same or different, each represents an alkyl group ($C_1$ to $C_{20}$), a cycloalkyl group ($C_3$ to $C_{10}$), an aralkyl group ($C_7$ to $C_{20}$) or an aryl group ($C_6$ to $C_{20}$) or, when taken together, $R_1$ and $R_2$ form a hetero ring, provided that $R_1$ and $R_2$ do not both represent an aryl group at the same time and $R_1$ and $R_2$ do not represent an aryl group and heterocyclic residue or heterocyclic residue and an aryl group, respectively, X represents a halogen atom (preferably Cl), and Ar represents an aryl group or a heterocyclic residue.

When the substituent represented by $R_1$ or $R_2$ in the above general formula (I) is an aryl group, it may have one or five substituents. Preferred examples of such substituent include an alkyl group ($C_1$ to $C_{12}$), an alkoxy group ($C_1$ to $C_{12}$), a halogen atom (preferably Cl), etc.

Preferred examples of $R_1$ or $R_2$ include an alkyl group containing 2 to 9 carbon atoms, a phenyl group, an alkyl ($C_1$ to $C_4$)-substituted aryl group, etc. The sum of the carbon atom numbers in $R_1$ and $R_2$ is preferably 4 to 18. Particularly preferably, both $R_1$ and $R_2$ represent alkyl groups.

The aryl group represented by Ar in the above general formula (I) may also have one or five substituents. Examples of such substituent include an alkyl group ($C_1$ to $C_{12}$), an alkoxy group ($C_1$ to $C_{12}$), a cyano group, a nitro group, a halogen atom (preferably Cl), an alkoxycarbonyl group ($C_2$ to $C_{12}$), an aryloxycarbonyl group ($C_7$ to $C_{12}$), an alkylcarbonyloxy group ($C_2$ to $C_{12}$), an arylcarbonyloxy group ($C_7$ to $C_{12}$), an alkylsulfonyloxy group ($C_1$ to $C_{12}$), an arylsulfonyloxy group ($C_6$ to $C_{12}$), a carbamoyl group, a sulfamoyl group, an alkylamino group ($C_1$ to $C_{12}$), a dialkylamino group ($C_2$ to $C_{24}$), an acylamino group ($C_2$ to $C_{12}$), an alkylsulfonylamino group ($C_1$ to $C_{12}$), an arylsulfonylamino group ($C_6$ to $C_{12}$), an alkylsulfonyl group ($C_1$ to $C_{12}$), an arylsulfonyl group ($C_7$ to $C_{12}$), an alkylcarbonyl group ($C_1$ to $C_{12}$), an arylcarbonyl group ($C_7$ to $C_{12}$), etc. These substituents may also be further substituted. Preferred examples of the aryl group represented by Ar include a phenyl group, an alkyl($C_1$ to $C_4$)-substituted phenyl group, an alkoxy($C_1$ to $C_4$)-substituted phenyl group, a halogen(e.g., Cl, Br, F, etc.)-substituted phenyl group, etc., with a phenyl group and an alkyl($C_1$ to $C_4$)-substituted phenyl group being particularly preferred.

As the heterocyclic ring residue represented by Ar in general formula (I), there may be illustrated a furyl group, a pyrrolyl group, a thienyl group, an indolyl group, a carbazolyl group, a phenoxazinyl group, a phenothiazinyl group, a phenazinyl group, etc., represented by the following formulae:

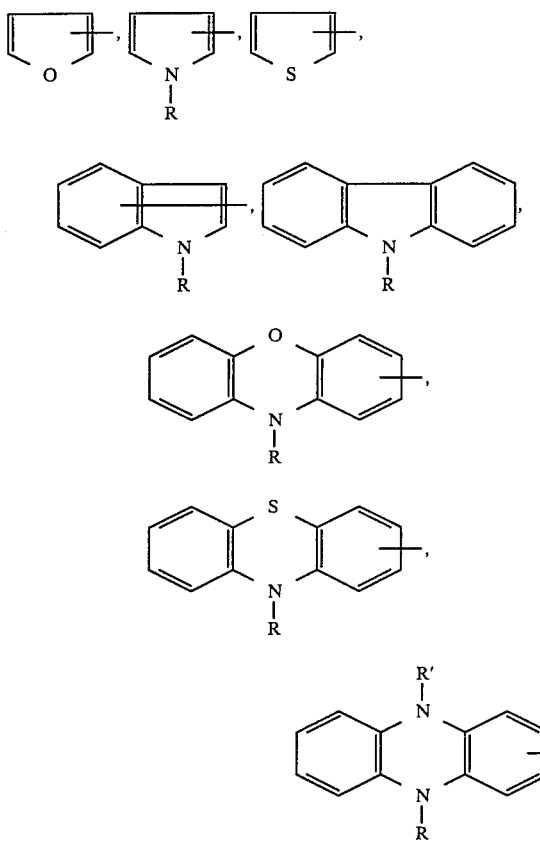

wherein R and R' each represents a hydrogen atom or an alkyl group ($C_1$ to $C_{12}$).

In general formula (I), benzene rings A and B may have substituents such as an alkyl group ($C_1$ to $C_{12}$), an alkoxy group ($C_1$ to $C_{12}$), a halogen atom, a nitro group, an amino group, an alkylamino group ($C_1$ to $C_{12}$), a dialkylamino group ($C_2$ to $C_{24}$), an acylamino group ($C_1$ to $C_{12}$), etc. Of these, an alkyl group containing 4 or less carbon atoms, an alkoxy group containing 4 or less carbon atoms and a halogen atom, are preferred.

In the above-described fluoran derivatives used in the present invention, the fluoran derivatives having the following general formula (II) are more preferred:

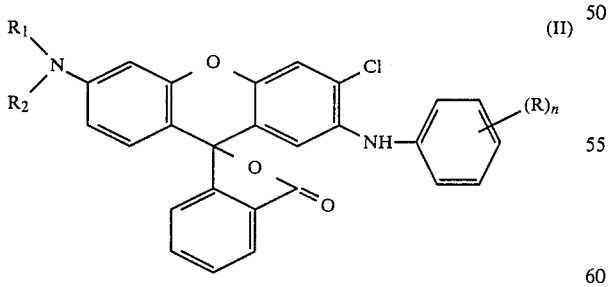

wherein substituents $R_1$ and $R_2$, which may be same or different, each represents an alkyl group ($C_2$ to $C_9$), substituent R represents an hydrogen atom, a chlorine atom or an alkyl group ($C_1$ to $C_4$), and n represents an integer of 1 to 3.

Further, the most preferred fluoran derivatives are as follows:

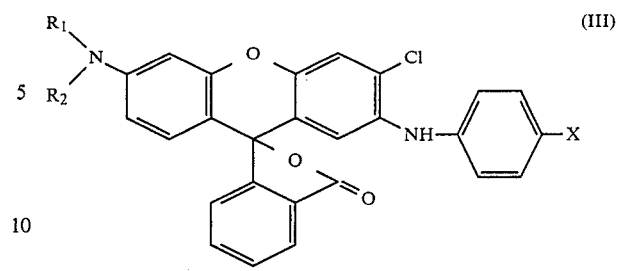

wherein substituents $R_1$ and $R_2$, which may be same or different, each represents an alkyl group ($C_2$ to $C_9$) and substituent X represents H, $CH_3$ or Cl.

All of the fluoran derivatives of the present invention are novel compounds and are usually colorless or slightly colored crystals and, when in contact with an electron accepting material, rapidly form a black color. As compared with dyes formed from conventional color formers, the dyes formed from the fluoran derivatives of the present invention are remarkably stable and undergo almost no discoloration or fading even when exposed to light, heated, or humidified for a long time, thus being particularly advantageous from the viewpoint of long-time storage. In addition, they themselves have such an excellent stability that they do not undergo change in properties or coloration and retain sufficient color-forming ability. Thus, they have nearly ideal properties as color formers for recording materials such as pressure-sensitive copying papers, heat-sensitive copying papers, etc.

Specific examples of the fluoran derivatives of the present invention are described below which, however, do not limit the present invention in any way.

(1) 2-Anilino-3-chloro-6-diethylaminofluoran
(2) 2-Anilino-3-chloro-6-dibutylaminofluoran
(3) 2-p-Anisidino-3-chloro-6-diethylaminofluoran
(4) 2-m-Anisidino-3-chloro-6-diethylaminofluoran
(5) 2-p-Toluidino-3-chloro-6-diethylaminofluoran
(6) 2-p-Chloroanilino-3-chloro-6-diethylaminofluoran
(7) 2-m-chloroanilino-3-chloro-6-diethylaminofluoran
(8) 2-p-Ethylanilino-3-chloro-6-diethylaminofluoran
(9) 2-p-Butylanilino-3-chloro-6-diethylaminofluoran Processes for synthesizing the fluoran derivatives of the present invention are described below.

The fluoran derivatives of the present invention can be prepared by a process shown by scheme A or scheme B. Moieties earlier used have the same meaning.

Scheme A

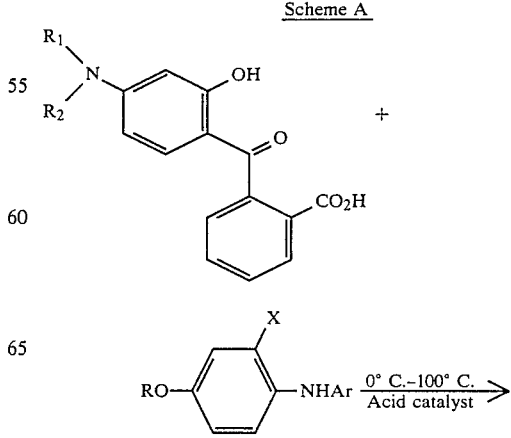

-continued
Scheme A

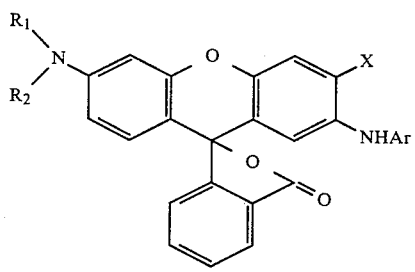

In the above scheme, R represents H,

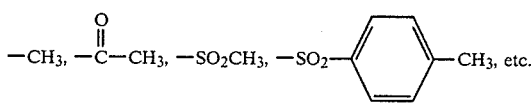

Scheme B

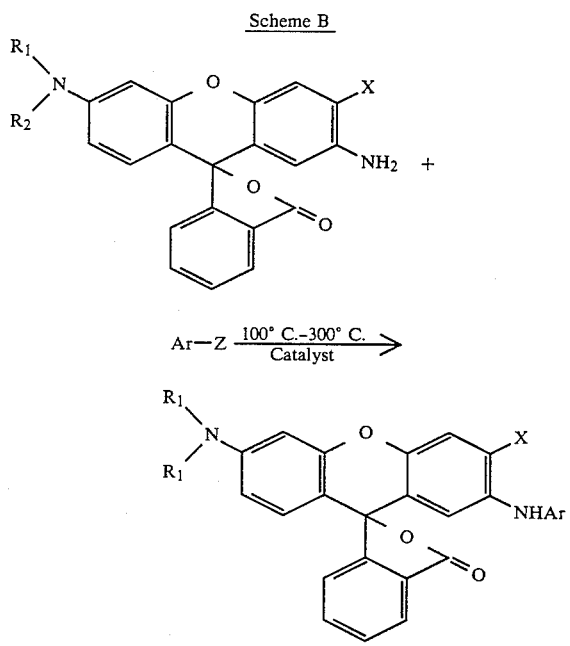

In the above scheme, Z represents a halogen atom (preferably BR and I) or a sulfonyloxy group represented by —OSO$_2$R$_5$, and R$_5$ represents an alkyl group (C$_1$ to C$_4$) or an aryl group (C$_6$ to C$_8$).

In scheme A, a benzoylbenzoic acid derivative is reacted with an arylaminophenol derivative in the presence of an acid catalyst.

As the acid catalyst, there can be used Lewis acids such as zinc chloride, aluminum chloride, magnesium chloride, etc., and Brnsted acids such as sulfuric acid, p-toluenesulfonic acid, methanesulfonic acid, etc.

On the other hand, in scheme B, a 2-aminofluoran derivative is reacted with an arylating agent in the presence of a catalyst.

As the catalyst used in scheme B, there are metallic copper powder, copper compounds such as cuprous iodide, cupric iodide, etc., nickel compounds, cobalt compounds, etc., with particulate metallic copper being particularly preferred.

Specific synthesis examples for several fluoran derivatives of the present invention are described below.

Unless otherwise indicated in the following examples, all pressures were atmospheric and all temperatures were room temperature.

SYNTHESIS EXAMPLE 1

Synthesis of 2-anilino-3-chloro-6-diethylaminofluoran (Compound (1))

A mixture of 6.2 g (0.02 mol) of 2-(2-hydroxy-4-diethylamino)benzoylbenzoic acid, 4.4 g (0.02 mol) of 3-chloro-4-anilinophenol, and 15 ml of concentrated 96% sulfuric acid was stirred at 40° C. for 10 hours. After cooling, the reaction solution was poured into ice water, neutralized with sodium hydroxide and extracted with ethyl acetate. After distilling off the solvent from the extract, the residue was purified using a silica gel column to obtain 6.8 g of 2-anilino-3-chloro-6-diethylaminofluoran (m.p. 179° to 180° C.).

SYNTHESIS EXAMPLE 2

Synthesis of 2-anilino-3-chloro-6-dibutylaminofluoran (Compound (2))

A mixture of 4.5 g (0.01 mol) of 2-amino-3-chloro-6-dibutylaminofluoran, 4.0 g (0.02 mol) of iodobenzene, 0.5 g of copper powder, potassium carbonate, and 10 ml of dimethylacetamide was stirred at not lower than 200° C. for 10 hours. After cooling, the reaction solution was poured into ice water, and extracted with ethyl acetate. After distilling of the solvent from the extract, the residue was purified using a silica gel column to obtain 3.0 g of 2-anilino-3-chloro-6-dibutylaminofluoran (m.p. 150° to 154° C.).

SYNTHESIS EXAMPLE 3

Synthesis of 2-p-toluidino-3-chloro-6-diethylaminofluoran (Compound (5))

A mixture of 6.2 g (0.02 mol) of 2-(2-hydroxy-4-diethylamino)benzoylbenzoic acid, 4.7 g (0.02 mol) of 3-chloro-4-p-toluidinophenol, and 15 ml of concentrated 96% sulfuric acid was stirred at 50° C. for 10 hours. After cooling, the reaction solution was poured into ice water, neutralized with sodium hydroxide, and extracted with ethyl acetate. After distilling off the solvent from the extract, the residue was purified using a silica gel column to obtain 7.0 g. of 2-p-toluidino-3-chloro-6-diethylaminofluoran (m.p. 184° to 185° C.).

The color hue of some typical fluoran derivatives of the present invention on activated clay are tabulated in Table 1.

TABLE 1

| Compound No. | Hue on Activated Clay |
| --- | --- |
| 1 | black |
| 2 | black |
| 3 | black |
| 5 | black |
| 6 | black |
| 7 | black |

A process for producing recording materials using the dye precursor of the present invention is described below.

Pressure-sensitive copying papers using the dye precursors of the present invention can be in various forms as described in U.S. Pat. Nos. 2,505,470, 2,505,471, 2,505,489, 2,548,366, 2,712,507, 2,730,456, 2,730,457, 3,418,250, etc. That is, they can be made by dissolving the above-described dye precursors alone or as a combination of two or more thereof or in combination with other dye precursors in a conventional solvent (a synthetic coil such as an alkylated naphthalene, an alkylated diphenyl, a diphenylalkane, an alkylated terphenyl or the like; a vegetable oil such as cotton seed oil, castor oil or the like; an animal oil; a mineral oil; a mixture thereof, etc.), dispersing the same in a conventional binder of microencapsulating the resulting solution, then coating on a support such as paper, a plastic sheet, a resin-coated paper or the like.

The amount of dye precursor used may be selected according to the desired thickness of the coating, the form of the pressure-sensitive copying paper, the process for preparing the microcapsules, etc. and it will be easy for one skilled in the art to set the amount. In microencapsulating the dye precursor, conventional processes may be employed, e.g., coacervation of a hydrophilic colloid sol as described in U.S. Pat. Nos. 2,800,457 and 2,800,458, interfacial polymerization as described in British Pat. Nos. 867,797, 950,443, and 1,091,076, and the like.

A general process for producing a heat-sensitive recording paper using a dye precursor of the present invention is described below.

That is, the dye precursor(s), an electron accepting material, and a heat meltable substance (used when the dye precursor or the electron accepting substance is not melted at the desired temperature) are pulverized and mixed in a solution of a solvent or a dispersion medium containing a binder dissolved or dispersed therein, and the resulting mixture is coated on a support such as paper, a plastic sheet, a resin-coated paper or the like. In preparing the mixture solution, all of the ingredients may be simultaneously mixed and pulverized or, alternatively, suitable combination thereof may separately be pulverized and dispersed, followed by mixing the resulting mixtures/solutions.

The coating solution of the mixture may also be incorporated in a support.

Further, an opacifying agent may be added thereto upon mixing.

The amounts of ingredients constituting a heat-sensitive recording paper are: 1 to 2 parts by weight of dye precursor: 1 to 6 parts by weight of electron accepting material; 0 to 30 parts by weight of heat meltable substance; 1 to 15 parts by weight of binder; and 20 to 300 parts by weight of dispersion medium (or solvent).

As the dye precursor, one or more of the fluoran derivatives of the present invention are used, with other known color formers for pressure-sensitive copying paper such as crystal violet lactone or a known fluoran derivative being optionally used.

As the electron accepting material, an acid clay (e.g., activated clay, terra abla, attapulgite, etc.), an organic acid (e.g., salicylic acid, tannic acid, gallic acid, a phenolic compound), metal salt thereof (e.g., a polyvalent metal salt of an aromatic carboxylic acid) preferably zinc salt, an acidic polymer such as a phenolformaldehyde resin, phenol resin or bisphenol A are preferred. The organic acids or the metal salts thereof are particularly preferred.

The dispersion medium (or solvent) must not substantially dissolve the dye precursor and the electron accepting material. If it does, a premature coloration takes place.

Therefore, water is most preferred as the dispersion medium (or solvent) used. Other usable materials include hydrocarbons such as hexane, ligroin, petroleum ether, etc.

The binder used in the present invention are conventional; there can be illustrated styrene-butadiene copolymers, alkyd resins, polybutyl methacrylate, vinyl chloride-vinyl acetate copolymers, styrene-maleic anhydride copolymers, synthetic rubbers, gum arabic, polyvinyl alcohol, hydroxyethyl cellulose, etc.

In view of the relationship with the dispersing medium (solvent), water-soluble binders such as gum arabic, polyvinyl alcohol, hydroxymethyl cellulose, etc. are preferred.

As the heat meltable substance, there can be used stearic acid amide, erucic acid amide, oleic acid amide, ethylene-bis-stearamide, benzoin, $\alpha$-naphthol, $\beta$-naphthol, p-t-butylphenol, p-phenylphenol, 4,4'-cyclohexylidenediphenol, 4,4'-isopropylidenediphenol, phthalic anhydride, maleic anhydride, stearic acid, erucic acid, palmitic acid, methyl p-hydroxybenzoate, diphenyl phthalate, triphenyl phosphate, p-hydroxydiphenyl ether, 2,2-bis{4-($\beta$-hydroxyethoxy)phenyl}propane, p-bis($\beta$-hydroxyethoxy)benzene, etc. Preferred examples of the heat meltable substance are that having a melting point of 50° to 200° C., more preferably 70° to 150° C.

These substances are colorless or slightly colored solids at ordinary room temperature and have a sharp melting point at copying temperatures, e.g., about 50° to about 180° C., and in the molten state, dissolve at least one, and preferably both, of the dye precursor and the electron accepting material.

Energizable heat-sensitive recording papers using the dye precursor of the present invention are obtained by coating on a support (such as paper) a solution prepared by dispersing a conductive material, a dye precursor, and an electron accepting material together with a binder in a dispersion medium (such as water) which does not substantially dissolve the dye precursor and the electron accepting material, or by first coating the conductive material on a support to form a conductive layer, and then coating thereon a solution prepared by dispersing a dye precursor and an electron accepting material with a binder in water or the like, as described in Japanese Patent Applications (OPI) 11344/74 and 48930/75 (the term "OPI" as used herein refers to a "published unexamined Japanese patent application"). Additionally, where both the dye precursor and the electron accepting material are not melted at a desired temperature (generally 70° to 120° C.), a heat meltable substance which is melted at the desired temperature to dissolve at least one of the dye precursor and the electron accepting material may be added to the coating solution to adjust sensitivity to Joule's heat generated by the energy added.

As the electron accepting material and the heat meltable material, those as described with respect to the heat-sensitive recording paper can be used.

Light-sensitive recording sheets of the present invention can be produced using the fluoran derivatives of the present invention in place of dye precursors such as lactone, lactam, spiropyran, carbinol, ethylene, leucoauramine, and oxazine compounds, etc. as are used in Japanese Patent Publications 24188/63, 10550/70, 13258/70, 204/74, 6212/74, 28449/74, Japanese Patent Applications (OPI) 31615/72, 32532/73, 9227/74, 135617/74, 80120/75, 87317/75, 126228/75, etc.

Other recording materials can similarly be produced by replacing conventionally used dye precursors with the fluoran derivatives of the present invention.

The present invention will now be described in more detail by reference to examples of preferred embodiments of the present invention which, however, are not to be construed as limiting the present invention in any way.

EXAMPLE 1

1 part (by weight, hereinafter the same applies) of the dye precursor Compound (1) in Table 1 was dissolved in 30 parts of alkylated naphthalene (the mixture of the various alkylated compounds which is mainly composed of diisopropyl naphthalene). The resulting solution was added, with vigorous stirring, to 50 parts by water containing 6 parts of gelatin and 4 parts of gum arabic to emulsify the same, oil droplets of $1\mu$ to $10\mu$ in diameter thus being formed. Then 250 parts of water was added thereto and the pH of the solution was adjusted to about 4 by gradually adding acetic acid to cause coacervation and form a gelatin-gum arabic capsule around the oil droplets. After adding formalin thereto, the pH of the system was raised to 9 with NaOH to harden the wall.

The thus prepared microcapsule dispersion was coated on paper and dried at about 50° C. When this paper was brought into contact with a paper coated with an acid clay (activated clay, terra abla or attapulgite), a phenol resin, 4,4'-isopropylidenediphenol, zinc 3,5-bis(α-methylbenzyl)salicylate, zinc p-toluenesulfonate or 2,2'-methylenebisphenol and pressure or impact was applied thereto, black images were instantly obtained. The thus formed images had high density and excellent light- and heat-resistance.

EXAMPLE 2

In the same manner as in Example 1 except for using the dye precursor Compound (6) shown in Table 1 in place of the dye precursor used in Example 1, there was prepared a microcapsule-coated paper. This paper provided a pressure-sensitive copying paper which rapidly formed color images of high density and excellent light- and heat-resistance.

EXAMPLE 3

30 parts of the dye precursor Compound (1) in Table 1 was mixed and pulverized for 2 hours with 150 parts of a 10% polyvinyl alcohol (a polymerization degree of 1700 and a saponification degree of 98%) aqueous solution and 70 parts of water to prepare a dispersion. The particle size after the pulverization was about $5\mu$ (ingredient A).

On the other hand, 30 parts of bisphenol A (4,4'-isopropylidenediphenol) and 30 parts of acetanilide were mixed and pulverized for 2 hours with 150 parts of a 10% polyvinyl alcohol (a polymerization degree of 1700 and a saponification degree of 98%) aqueous solution and 55 parts of water to prepare a dispersion. The particle size of insoluble material after the pulverization was about $5\mu$ (ingredient B).

Then, 5 parts of ingredient A was mixed with 40 parts of ingredient B, and the resulting mixture was coated on paper and dried at 50° C. to obtain a heat-sensitive recording paper.

This heat-sensitive recording paper formed black images when heated by a hot pen or the like. When this heat-sensitive recording paper was superposed on an original and heated in a heat copier, there was obtained a black copy which was extremely stable to light and scarcely changed in color hue and density, even when irradiated with an ultraviolet ray lamp for one hour.

While the invention has been described in detail and with reference to specific embodiments thereof, it will be apparent to one skilled in the art that various changes and modifications can be made therein without departing from the spirit and scope thereof.

What is claimed is:

1. A recording material comprising a support onto which is coated or into which is incorporated a fluoran derivative having an arylamino group at the 2-position of the fluoran skeleton thereof and a halogen atom at the 3-position of the fluoran skeleton thereof, wherein the fluoran derivative has the following Formula (II):

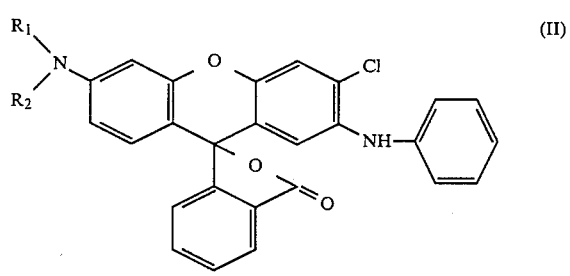

wherein $R_1$ and $R_2$, which may be the same or different, each represents an alkyl group having 2 to 9 carbon atoms, and the fluoran derivative forms a black image.

2. A recording material as in claim 1, wherein said recording material is a pressure-sensitive recording material or a heat-sensitive recording material.

3. A recording material as in claim 1, wherein the fluoran derivative has the following Formula (III):

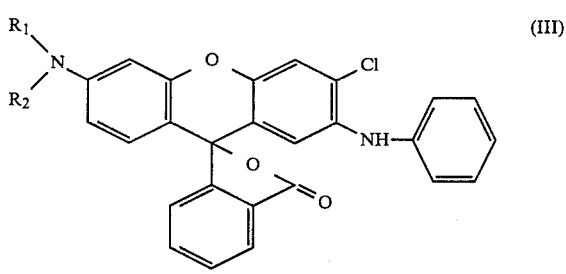

wherein $R_1$ and $R_2$, which may be the same or different, each represents an alkyl group having 2 to 9 carbon atoms and the fluoran derivative forms a black image.

4. A recording material as in claim 3, wherein said recording material is a pressure-sensitive recording material or a heat-sensitive recording material.

* * * * *